(12) United States Patent
Chen

(10) Patent No.: US 11,311,281 B2
(45) Date of Patent: Apr. 26, 2022

(54) OCCLUDER AND OCCLUSION DEVICE

(71) Applicant: LIFETECH SCIENTIFIC (SHENZHEN) CO., LTD, Shenzhen (CN)

(72) Inventor: Xianmiao Chen, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 132 days.

(21) Appl. No.: 16/493,985

(22) PCT Filed: Mar. 7, 2018

(86) PCT No.: PCT/CN2018/078276
§ 371 (c)(1),
(2) Date: Sep. 13, 2019

(87) PCT Pub. No.: WO2018/184438
PCT Pub. Date: Oct. 11, 2018

(65) Prior Publication Data
US 2020/0121306 A1 Apr. 23, 2020

(30) Foreign Application Priority Data
Apr. 6, 2017 (CN) .......................... 201710226942.5

(51) Int. Cl.
*A61B 17/00* (2006.01)
(52) U.S. Cl.
CPC .............................. *A61B 17/0057* (2013.01); *A61B 2017/00606* (2013.01); *A61B 2017/00619* (2013.01);
(Continued)
(58) Field of Classification Search
CPC ...... A61B 17/0057; A61B 2017/00606; A61B 2017/0619; A61B 2017/00623
See application file for complete search history.

(56) References Cited

U.S. PATENT DOCUMENTS 5,171,259 A * 12/1992 Inoue ................. A61B 17/0057
606/213
2005/0273135 A1* 12/2005 Chanduszko ...... A61B 17/0057
606/213
(Continued)

FOREIGN PATENT DOCUMENTS

CN 103654883 A 3/2014
CN 104287803 A 1/2015
(Continued)

OTHER PUBLICATIONS

International Search Report dated Jun. 5, 2018 in corresponding International Application No. PCT/CN2018/078276; 4 pages.
(Continued)

*Primary Examiner* — Alexander J Orkin
(74) *Attorney, Agent, or Firm* — Maier & Maier, PLLC

(57) ABSTRACT

An occluder and an occlusion device, including: a mesh occlusion body, which defines a cavity, and a proximal end bolt head; the proximal end bolt head configured with a locking hole which penetrates the cavity; the occluder further having a locking member, a distal end of the locking member being connected to a distal end of the occlusion body; the locking member having a connecting portion which is connected to the occlusion body; the diameter of a circumscribed circle of a projection of the first bending portion on a cross section perpendicular to a length direction thereof being smaller than the diameter of the smallest inscribed circle of a locking hole, and the width of a projection of the first bending portion on a plane perpendicular to longitudinal central axis direction of the locking hole being larger than the diameter of the largest inscribed circle of the locking hole.

14 Claims, 7 Drawing Sheets

(52) U.S. Cl.
CPC ............... *A61B 2017/00623* (2013.01); *A61B 2017/00867* (2013.01)

(56) References Cited

U.S. PATENT DOCUMENTS

| | | |
|---|---|---|
| 2006/0122647 A1 | 6/2006 | Callaghan et al. |
| 2007/0167981 A1* | 7/2007 | Opolski ............. A61B 17/0057 606/213 |
| 2007/0244517 A1* | 10/2007 | Callaghan .......... A61B 17/0057 606/213 |
| 2012/0078295 A1* | 3/2012 | Steiner ............... A61B 17/0057 606/213 |
| 2013/0289618 A1 | 10/2013 | Chanduszko et al. |
| 2014/0343602 A1* | 11/2014 | Cox ................. A61B 17/12113 606/215 |

FOREIGN PATENT DOCUMENTS

| | | |
|---|---|---|
| CN | 204181658 U | 3/2015 |
| EP | 1169968 A1 | 1/2002 |
| WO | 2007/092274 A1 | 8/2007 |

OTHER PUBLICATIONS

Indian Office Action dated Jul. 30, 2021, in connection with corresponding IN Application No. 201917044283.

* cited by examiner

OCCLUDER AND OCCLUSION DEVICE

FIELD

The present application relates to an interventional medical instrument, and more particularly relates to an occluder and an occlusion device for interventionally treating congenital heart diseases.

BACKGROUND

Percutanerus intervention is a disease treatment measure developed rapidly in recent years and is applied more and more extensively. All kinds of materials, instruments and drugs may be placed into a human heart and arteriovenous vessels by an interventional catheterization method. The instruments may be a heart defect occluder, a vascular plug, a vascular filter and the like.

A transcatheter interventional occluder is an instrument commonly used in the interventional catheterization method, and may be used for minimally invasively treating congenital heart diseases such as an atrial septal defect, an ventricular septal defect, patent ductus arteriosus and patent foramen ovale. An occluder in the prior art generally includes an occlusion body having two occlusion units to cover tissues on two side walls of a defect part. However, most known occlusion units are made of memory metals which may possibly have a fatigue failure during use or macromolecular materials which have low elasticity or no elasticity, which results in insufficient contractility between two occlusion units and influence on an occlusion effect caused by a failure of clinging to the two sides of the defect part. Therefore the occluder needs an effective restraint structure to keep a distance (namely the waist height of the occluder) between the two occlusion units, in order to guarantee the occlusion reliability.

SUMMARY

The present application provides an occluder having a locking function and an occlusion device to solve the technical problems and overcome the shortcomings in the prior art.

To solve the technical problems, an exemplary embodiment of the present application is as follows:

an occluder, including a mesh occlusion body defining a cavity and a proximal end bolt head. The proximal end bolt head has a locking hole communicated with the cavity. The occluder further includes a locking member located in the cavity. The distal end of the locking member is connected with the distal end of the occlusion body. The locking member is an elastic member, and includes a connecting portion connected with the occlusion body and a first bending portion connected with the proximal end of the connecting portion. A joint of the connecting portion and the first bending portion has a first bending included angle. The diameter of a circumscribed circle of a projection of the first bending portion on a cross section perpendicular to the lengthwise direction of the first bending portion is less than that of a minimum inscribed circle of the locking hole. The width of a projection of the first bending portion on a plane perpendicular to the longitudinal central axis direction of the locking hole is greater than the diameter of a maximum inscribed circle of the locking hole.

In an exemplary implementation mode of the present application, the occluder includes a mesh occlusion body defining a cavity and a proximal end bolt head. The proximal end bolt head has a locking hole communicated with the cavity. The occluder further includes a locking member located in the cavity. The distal end of the locking member is connected with the distal end of the occlusion body. The locking member is an elastic member, and includes a connecting portion connected with the occlusion body and a plurality of bending portions connected with one another end to end. The proximal ends of the end-to-end bending portions are connected with the proximal end of the connecting portion, and a first bending included angle is formed between the connecting portion and the bending portion closest to the connecting portion. The diameter of a circumscribed circle of a projection of each bending portion on a cross section perpendicular to the lengthwise direction of the bending portion is less than that of a minimum inscribed circle of the locking hole. The width of a projection of a hole, formed by the multiple end-to-end bending portions, on a plane perpendicular to the longitudinal central axis direction of the locking hole is greater than the diameter of a maximum inscribed circle of the locking hole.

In a further embodiment, an occlusion device is provided, including a hollow delivery mechanism at least provided with an opening in the distal end, a locking sleeve for connecting the delivery mechanism with the occluder, and a traction member movably accommodated in the delivery mechanism. The distal end of the traction member penetrates the distal end of the delivery mechanism and then is detachably connected with the proximal end of the bending portion of the locking member.

In the occluder of the present application, a locking process may be completed by the cooperation of the locking member and the proximal end bolt head having the locking hole, the structure is simple and the locking operation is simplified. The locking member of the present application is elastic, and includes the connecting portion and the first bending portion, and the bending included angle is formed between the connecting portion and the first bending portion. According to the present application, in processes of locking and unlocking the locking mechanism, it is only required to control the width of the projection of the first bending portion on the plane perpendicular to the longitudinal central axis direction of the locking hole to be greater than the diameter of the maximum inscribed circle of the locking hole and control the diameter of the circumscribed circle of the projection of the first bending portion on the cross section perpendicular to the lengthwise direction of the first bending portion to be less than that of the minimum inscribed circle of the locking hole, and the width of the projection of the first bending portion on the plane perpendicular to the longitudinal central axis direction of the locking hole is mainly determined by the bending included angle, so it only needs to control the size of the bending included angle and the diameter of the circumscribed circle of the projection of the first bending portion on the cross section perpendicular to the lengthwise direction of the first bending portion instead of controlling the size accuracy between the locking member and the locking hole of the present application at a micron level. During machining, the bending included angle between the connecting portion and the first bending portion is easy to control, and at the same time, during the design, the locking member may be designed to be smaller to reserve a certain size to effectively prevent a locking failure of the occluder resulted from a size change caused by swelling of the macromolecular material. Therefore, the present application is simple in structure, and the size of the locking member is easy to control, thus facilitating the machining and simplifying a manufacturing process and the locking operation. In addition, the locking member is difficult to fail thanks to its high locking reliability, and furthermore, the locking operation process is reversible, and the locking process and a withdrawing process are simple and feasible.

The overall locking member of the present application is a bent tube, and the sizes of all the parts are matched to effectively reduce the size of the locking member and prevent the influence on contraction and resilience of the occluder caused by a certain oversized part of the locking member.

The traction member is detachably connected with the locking member of the above-mentioned occluder, and is convenient for controlling connection or disconnection, so that an operability of the connection between the traction member and the occluder is improved; and after the locking is completed, the traction member may be disconnected and withdrawn out of the body to reduce remaining in the body. In addition, the traction member does not need to pass through the distal end of the occluder, so as to avoid harm to heart tissues, shorten the occlusion operation time and improve the operation efficiency. Furthermore, the locking member is only fixed with the distal end of the occlusion body, and the setting direction of the locking member is the same as the direction of a sheath tube, so that the structure and the fixing mode of the locking member do not affect the deformation of the occluder in a delivery sheath tube and the occlusion of the occluder pushed to a position for the defect part. The size of the delivery sheath is only required to be matched with that of an occluder without extra increase, which is favorable for the surgery.

BRIEF DESCRIPTION OF THE DRAWINGS

The present application will be further described below in combination with accompanying drawings and embodiments. In the drawings.

DETAILED DESCRIPTION OF THE EMBODIMENTS

To understand the technical features, objectives and effects of the present application more clearly, specific implementation modes of the present application are described now in detail in combination with accompanying drawings.

To describe the structure of the present application more clearly, "distal end" and "proximal end" are used as localizers. The localizers are terms commonly used in the field of interventional medical instruments. The "distal end" refers to the end away from an operator in the surgical procedure, and the "proximal end" refers to the end close to the operator in the surgical procedure. The axial direction refers to a direction parallel to a connecting line between the center of the distal end of a medical instrument and the center of the proximal end of the medical instrument. The radial direction refers to a direction perpendicular to the axial direction.

Figure 1:
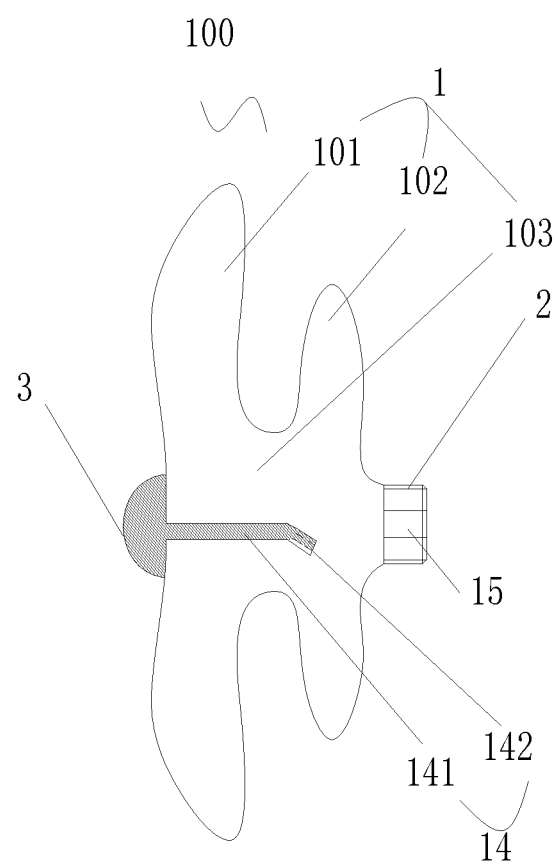
FIG. 1 is a structural schematic diagram of an occluder provided in a first exemplary embodiment of the present application.

In a first exemplary embodiment, referring to FIG. 1, an occluder 100 includes a mesh occlusion body 1 defining a cavity 103, a proximal end bolt head 2, and a distal end seal head 3. The proximal end bolt head 2 is fixedly connected to the proximal end of the occlusion body 1, and the distal end seal head 3 is fixedly connected to the distal end of the occlusion body 1. The occlusion body 1 includes a first occlusion unit 101 and a second occlusion unit 102 which are both disk-shaped, and the two occlusion units 101 and 102 are in communication to form an "I" shape. The occluder 100 further includes a locking member 14 located in the cavity 103. The distal end of the locking member 14 is connected with the distal end of the occlusion body 1. The proximal end bolt head 2 defines a locking hole 15 communicated with the cavity 103. In an example, the locking hole 15 is coaxial with the proximal end bolt head 2.

It can be understood that the structure of the occlusion body 1 is only used as an example, but not intended to limit the present application. Those of ordinary skill in the art can select any proper structure for an occlusion body 1 under the inspiration of the present application. The mesh structure is easy to deform, is convenient for effectively compressing the occluder 100 into a sheath tune in a delivery process, and is also convenient for deformation into two disk-shaped structures favorable for defect occlusion when the occluder is pushed out of the sheath tube and arrives at a defect part.

The locking member 14 includes a connecting portion 141 and a first bending portion 142 connected with the proximal end of the connecting portion 141. A preset bending included angle A is formed between the connecting portion 141 and the first bending portion 142. The locking member 14 is elastic and may elastically deform under the action of an external force. That is, under the action of the external force, the first bending included angle A between the connecting portion 141 and the first bending portion 142 may vary; and after the external force disappears, the first bending included angle A between the connecting portion 141 and the first bending portion 142 recovers to the original angle.

The diameter of a circumscribed circle of a projection of the first bending portion 142 on the cross section perpendicular to a lengthwise direction of the first bending portion 142 is less than that of a minimum inscribed circle of the locking hole 15. In one example, referring to FIG. 3 together, in the present embodiment, the locking member 14 is of a columnar structure having a circular cross section. At the moment, the outer diameter d of the first bending portion 142 is the diameter of the circumscribed circle of the projection of the first bending portion 142 on the cross section perpendicular to the lengthwise direction of the first bending portion 142. It can be understood that in other embodiments, the locking member 14 may be of a structure having an elliptical cross section, a trapezoid cross section or a cross section of other shapes.

Figure 2:
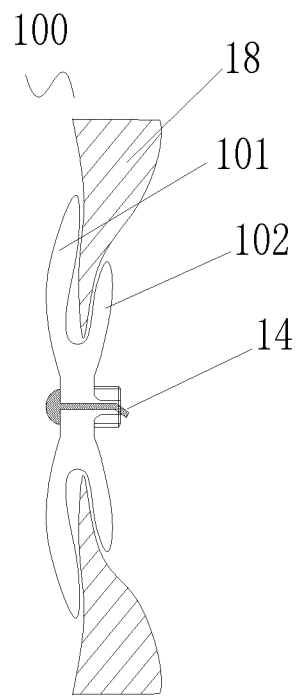
FIG. 2 is a schematic diagram of a locked state of the occluder provided in a first exemplary embodiment of the present application.
Figure 3:
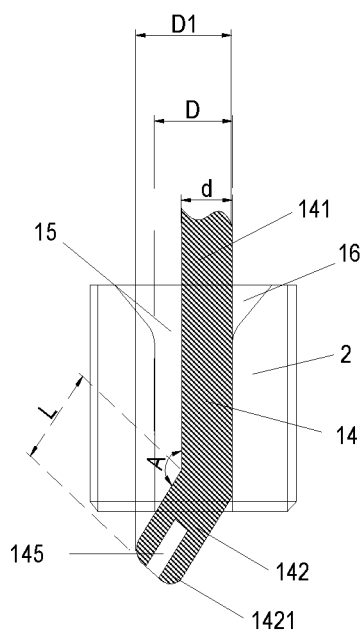
FIG. 3 is a partial structural schematic diagram of locking a locking member and a proximal end bolt head of the occluder in FIG. 2.

Referring to FIG. 2 and FIG. 3, in the present embodiment, the locking hole 15 is a cylindrical hole. The diameter of a maximum inscribed circle of the locking hole 15 is equal to that of the minimum inscribed circle, and the inner diameter D of the locking hole 15 is the diameter of its maximum inscribed circle and the diameter of its minimum inscribed circle. The proximal end of the first bending portion 142 may be inserted into the locking hole 15 and passes through the proximal end of the locking hole 15. The width of a projection of the first bending portion 142 on a plane perpendicular to the longitudinal central axis direction of the locking hole 15 is greater than the diameter of the maximum inscribed circle of the locking hole 15. The width of the projection refers to a distance between two farthest points on the projection of the first bending portion 142 on the plane perpendicular to the longitudinal central axis of the locking hole 15. In the present embodiment, the width of the projection of the first bending portion 142 on the plane perpendicular to the longitudinal central axis direction of the locking hole 15 is D1. After the first bending portion 142 passes through the locking hole 15, the locking member 14 and the locking hole 15 are locked in the absence of the external force.

It can be understood that in other embodiments, the locking hole 15 also may be a conical hole, a gourd-shaped hole, a quadrangular hole, and the like, as long as the diameter of the minimum inscribed circle of the locking hole 15 is greater than that of the circumscribed circle of the projection of the first bending portion 142 on the cross section perpendicular to the lengthwise direction of the first bending portion 142, and the width of the projection of the first bending portion 142 on the plane perpendicular to the longitudinal central axis direction of the locking hole 15 is greater than the diameter of the maximum inscribed circle of the locking hole 15.

Further, the occluder 100 has a natural state and a locked state. In the natural state which is an external force-free state, as shown in FIG. 1, the first occlusion unit 101 and the second occlusion unit 102 of the occluder 100 are away from each other, and the proximal end of the locking member 14 is not inserted into the locking hole 15. The outer diameter d of the first bending portion 142 of the locking member 14 is less than the inner diameter D of the locking hole 15. In an example, the overall width of the locking member 14 is kept consistent.

Referring to FIGS. 1 to 3 together, when moving towards the proximal end under the action of an external force, that is, when changed from the natural state into the locked state as shown in FIG. 2, the locking member 14 drives the distal end of the occlusion body 1 to move towards the proximal end bolt head 2. As the outer diameter d of the first bending portion 142 is less than the inner diameter D of the locking hole 15, the proximal end of the first bending portion 142 may be inserted into the locking hole 15. Along with the insertion of the locking member 14, a force may be generated between the first bending portion 142 of the locking member 14 and the inner wall of the locking hole 15, and the first bending portion 142 bends under the pressing action of the inner wall of the locking hole 15, so that the first bending included angle A is enlarged to allow D1 of the projection of the first bending portion 142 on the plane perpendicular to the longitudinal central axis of the locking hole 15 to be less than or equal to the inner diameter D of the locking hole 15 and allow the first bending portion 142 to be continuously inserted into the locking hole 15. When the distal end of the first bending portion 142 is exposed from the distal end of the locking hole 15, the force from the inner wall of the locking hole 15 to the first bending portion 142 disappears gradually, and the first bending portion 142 gradually recovers its original shape. When the locking member 14 continuously moves towards the proximal end, the first bending included angle A is continuously decreased. When the external force pulling the locking member 14 to move towards the proximal end disappears, as the width D1 of the first bending portion 142 on the plane perpendicular to the longitudinal central axis of the locking hole 15 is greater than the inner diameter D of the locking hole 15, the side surface of the first bending portion 142 abuts against the proximal end face of the locking hole 15 to prevent the locking member 14 from moving towards the distal end to complete the locking of the locking member 14, so that the two occlusion units 101 and 102 may not rebound under the action of their elasticity and may be continuously kept closed up.

The above-mentioned external force pulling the locking member may be a traction force applied by a doctor (or other party charged with manipulating the device) to the locking member 14 towards the proximal end. In the locked state, the distance between the first occlusion unit 101 and the second occlusion unit 102 of the occlusion body 1 is constant (namely the waist height of the occlusion body is constant).

In the present embodiment, to better complete the above-mentioned operation, all the components of the occluder 100 have some desired or predetermined sizes. For example, the occluder 100 is delivered into the body by an interventional method, so that the size of the proximal end bolt head 2 of the occluder 100 may not be too large, which restrains the inner diameter D of the locking hole 15. Referring to FIG. 3, the inner diameter D of the locking hole 15 ranges between about 0.5 mm to 3 mm; the first bending included angle A between the connecting portion 141 and the first bending portion 142 of the locking member 14 ranges between about 120 degrees to 175 degrees; and the length L of the first bending portion 142 of the locking member 14 ranges between about 0.5 mm to 3 mm. The outer diameters d of the connecting portion 141 and the first bending portion 142 are less than the value of the inner diameter D of the locking hole 15, and the outer diameters d of the connecting portion 141 and the first bending portion 142 are equal, and a ratio of the outer diameter d to the inner diameter D of the locking hole 15 is about 0.5-0.95. A too-small ratio of the outer diameter d of the first bending portion 142 to the inner diameter D of the locking hole 15 may lead to unreliable locking, and a too-large ratio of the outer diameter d of the first bending portion 142 to the inner diameter D of the locking hole 15 may lead to a relatively high difficulty in inserting the first bending portion 142 into the locking hole 15. As the width D1 of the projection of the first bending portion 142 on the plane perpendicular to the longitudinal central axis of the locking hole 15 is greater than the inner diameter D of the locking hole 15, after the first bending portion 142 passes through the locking hole 15, the connecting portion 141 of the locking member 14 may be located in the locking hole 15 smoothly. In addition, while a heart is beating, the occluder 100 also may deform in a coordinated manner to adapt to the heart beating. That is, when the heart is beating, the width of the connecting portion 141 is less than the inner diameter D of the locking hole 15, and the connecting portion 141 still may move towards the proximal end of the occluder 100, so that the first occlusion unit 101 and the second occlusion unit 102 of the occluder 100 still may continuously get close to each other under the action of pressure along with the heart beating, and the occluder 100 may deform coordinately along with the heart beating.

The locking function of the occluder 100 is mainly implemented through the cooperation of the locking member 14 arranged in the cavity 103 of the occlusion body 1 and the locking hole 15 formed in the proximal end bolt head 2. The locking member 14 may be made of a metal material or a macromolecular material biologically compatible with a human body. The distal end of the locking member 14 is connected with the distal end of the occlusion body 1. Under the traction of an external force (such as a pulling force of a traction member), the locking member 14 may drive the distal end of the occlusion body 1 to move towards the proximal end.

FIG. 1 shows the non-locked natural state of the occluder 100, and FIG. 2 shows a state that the locked occluder 100 occludes a defect part 18.

The mesh structure of the occlusion body 1 may be manufactured by adopting a memory alloy material or a macromolecular material in a way of weaving, tubular product cutting, injection molding, or the like. The memory alloy material includes a nickel-titanium alloy, and the macromolecular material is good in biological compatibility. Compared with a metal material, the macromolecular material may avoid problems caused by a release of metal elements in the body, and a material having the good biological compatibility may effectively reduce infection risks of an occluded part. The occlusion body 1 in the present application may be woven from a degradable macromolecular wire which may be made of a similar material such as PET (Polyethylene Terephthalate), PLA (Poly-L-lactide Acid), PGA (Poly-glycolide), PHA (Poly-hydroxyalkanoate), PDO (Polu-dioxanone) and PCL (Poly-caprolactone).

Referring to FIG. 1 to FIG. 2 again, the distal end of the occlusion body 1 is further provided with the distal end seal head 3. The locking member 14 is connected with the distal end seal head 3. It can be understood that in other embodiments, the distal end of the occlusion body 1 also may be of a seal head-free structure. When an occluder 100 without a seal head structure at the distal end is adopted, the locking member 14 may be directly connected with the distal end of the occlusion body 1. When an occlusion body 1 of a grid structure woven from a weaving wire is adopted, the distal end seal head 3 and the proximal end bolt head 2 may be respectively arranged at the distal end and the proximal end to accommodate and fix the end portions of the weaving wires forming the mesh structure. There are no limitations to the shapes and the structures of the distal end seal head 3 and the proximal end bolt head 2. In the present embodiment, the distal end seal head 3 is a curved body, and the proximal end bolt head 2 is of a columnar structure.

Compared with a traditional memory alloy (such as a nickel-titanium alloy), the macromolecular material has the characteristics of relatively low elastic modulus and relatively small elasticity range, and the memory alloy may possibly have a fatigue failure during long-term use and may not effectively occlude the defect part. It is possible that by the adoption of the above-mentioned two materials, the occlusion body 1 may not be well kept in its predetermined shape after being set. At the moment, a locking structure is utilized to improve the forming performance of the occluder 100 in the human body. The present application correspondingly designs a locking structure, including the locking member 14 and the locking hole 15. The locking structure is applicable to locking the occlusion body 1 made of the macromolecular material and is also applicable to locking an occluder 100 made of other materials.

In the prior art, during implementation of locking and unlocking of two structures, there is a very high requirement on the size accuracy of the locking member, and the accuracy is generally required to be about 1 micron. It is relatively hard for the metal material to reach this accuracy, and it is harder for the macromolecular material to control this size accuracy. In addition, the locking member and the proximal end bolt head which are made of the macromolecular material are exposed to water during the cleaning and are exposed to blood during the operation. In these processes, the water-absorbing swelling property of the macromolecular material or the adsorption of biomolecules in the blood will affect the size accuracy of the macromolecular components and thus affect the locking function, namely a subtle change of the size may lead to difficult implementation of interference fit and may finally result in a surgical failure.

In an occluder of the present application, the locking process may be completed by the cooperation of the locking member and the proximal end bolt head having the locking hole, the structure is simple and the locking operation is simplified compared to the prior art. The locking member of the present application is elastic, and includes the connecting portion and the first bending portion, and the bending included angle is formed between the connecting portion and the first bending portion. According to the present application, in the processes of locking and unlocking the locking mechanism, it is only utilized to control the width of the projection of the first bending portion on the plane perpendicular to the longitudinal central axis direction of the locking hole to be greater than the diameter of the maximum inscribed circle of the locking hole and control the diameter of the circumscribed circle of the projection of the first bending portion on the cross section perpendicular to the lengthwise direction of the first bending portion to be less than that of the minimum inscribed circle of the locking hole, and the width of the projection of the first bending portion on the plane perpendicular to the longitudinal central axis direction of the locking hole is mainly determined by the bending included angle, so it only needs to control the size of the bending included angle and the diameter of the circumscribed circle of the projection of the first bending portion on the cross section perpendicular to the lengthwise direction of the first bending portion instead of controlling the size accuracy between the locking member and the locking hole of the present application at a micron level. During machining, the bending included angle between the connecting portion and the first bending portion is easy to control, and at the same time, during the design, the locking member is designed to be smaller to reserve a certain size to effectively prevent the locking failure of the occluder resulted from a size change caused by the swelling of the macromolecular material. Therefore, the present application is simple in structure, and the size of the locking member is easy to control, thus facilitating the machining and simplifying a manufacturing process and the locking operation. In addition, the locking member is difficult to fail thanks to its high locking reliability, and furthermore, the locking operation process is reversible, and the locking process and a withdrawing process are simple and feasible.

Referring to FIG. 3, the locking member 14 is detachably connected with a pusher or a pushing device, so that one of detachable connection modes may be threaded connection. The proximal end of the first bending portion 142 of the locking member 14 is configured with a threaded hole 145. In the present embodiment, the threaded hole 145 is coaxial with the first bending portion 142, and the coaxial threaded hole 145 may be connected with a pushing mechanism more easily.

It can be understood that in other embodiments, the locking member 14 also may adopt a hollow tube design. During production, the inner wall of the hollow tubular locking member 14 of a predetermined size is configured with an internal thread, and the locking member 14 is bent into a predetermined angle, so as to form the connecting portion 141 and the first bending portion 142. The hollow tubular locking member 14 may simplify the machining process and may easily control the coaxiality between the threaded hole and the first bending portion 142, so as to allow the locking member 14 to be connected with a traction device or the pushing device more easily.

It can be understood that in other embodiments, the proximal end of the locking member 14 also may be configured with no thread, but the locking member 14 also may be detachably connected with the traction device or the pushing device through a fastener.

It can be further understood that the connection between the locking member 14 and the traction device or the pushing device may be in other connection modes which are not listed one by one here, as long as the locking member 14 is detachably connected with the pusher or the pushing device.

Figure 4:
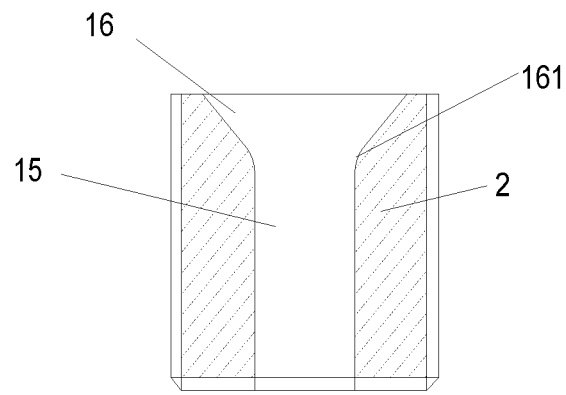
FIG. 4 is a structural schematic diagram of a locking hole of the occluder in FIG. 1.

Referring to FIG. 3 again, in order to insert the locking member 14 into the locking hole 15 of the proximal end bolt head 2 more easily, a fillet 1421 is added at the proximal end portion of the first bending portion 142 of the locking member 14. The fillet 1421 refers to that the proximal end face of the first bending portion 142 and the side wall of the first bending portion 142 are in arc transition and the outer diameter of the proximal end face is less than that of the side wall of the first bending portion 142. Correspondingly, referring to FIG. 4, a hollow transitional region 16 is arranged at a position, close to the distal end of the locking hole 15, of the locking hole 15. The radial length of the transitional region 16 is gradually increased from the proximal end to the distal end, and the transitional region 16 is communicated with the locking hole 15. As the fillet 1421 is arranged at the proximal end portion of the first bending portion 142, the first bending portion 142 is inserted into the conical transitional region 16 having a relatively large opening more easily, so as to enter the locking hole 15.

The whole transitional region 16 may be of a similar conical shape or horn shape. The radial length of the proximal end of the transitional region 16 is less than that of the distal end. It can be understood that in other embodiments, the transitional region 16 also may be of a similarly trapezoid shape. Or, in still other embodiments, when a difference between the radial lengths of the locking member 14 and the locking hole 15 is relatively large, no transitional region is set.

It can be further understood that in other embodiments, the edge of the proximal end of the transitional region 16 is configured with an arc-shaped chamfer 161 which may cooperate with the fillet 1421 on the locking member 14. When the locking member 14 moves towards the proximal end under the traction of an external force, the arc-shaped chamfer 161 may avoid the edge of the proximal end of the transitional region 16 from abutting against the proximal end of the locking member 14, so as to allow the locking member 14 to be inserted into the locking hole 15 more easily.

Figure 5:
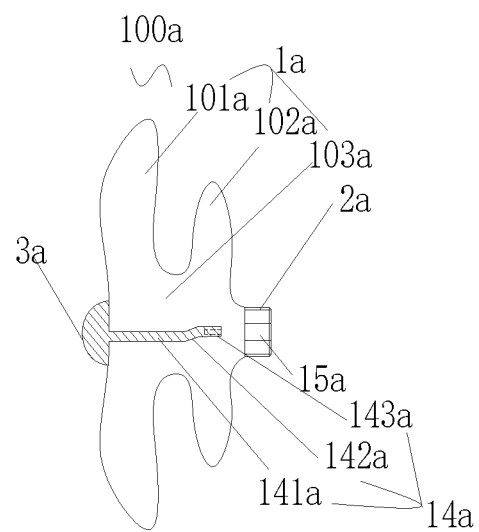
FIG. 5 is a structural schematic diagram of an occluder of a second exemplary embodiment of the present application.

In a second exemplary embodiment, referring to FIG. 5, the present application further shows an occluder 100a. The occluder 100a is substantially similar to occluder 100 shown by the first embodiment, and a difference lies in that in this embodiment, a locking member 14a of the occluder 100a includes a connecting portion 141a, a first bending portion 142a and a second bending portion 143a. The proximal end of the connecting portion 141a is connected with the distal end of the first bending portion 142a, and the proximal end of the first bending portion 142a is connected with the distal end of the second bending portion 143a.

Figure 6:
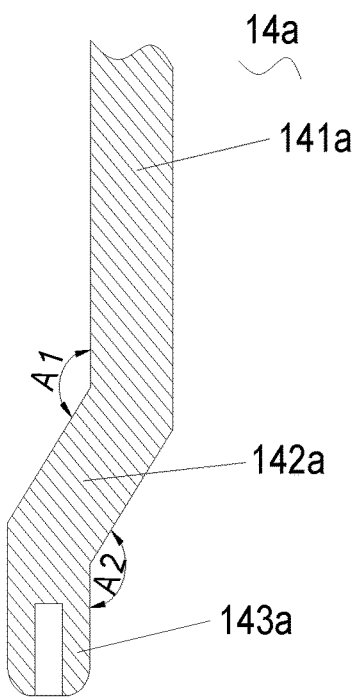
FIG. 6 is a structural schematic diagram of a locking member of the occluder in FIG. 5.

Referring to FIG. 6 as well, a first bending included angle A1 is formed between the first bending portion 142a and the connecting portion 141a, and a second bending included angle A2 is formed between the first bending portion 142a and the second bending portion 143a. In an example, the first bending included angle A1 and the second bending included angle A2 are equal, in order to ensure that the connecting portion 141a and the second bending portion 143a are kept in a parallel state, thereby keeping an acting direction of a force of the locking member 14a under the pulling of an external force unchanged, and facilitating the connection of the locking member 14a and a traction device; and, in addition, the proximal end of the locking member 14a may be inserted into a locking hole 15a more easily.

It can be understood that in other embodiments, the first bending angle A1 also may be different from the second bending angle A2 as long as the width of a projection of a hole formed by the first bending portion 142a and the second bending portion 143a on a plane perpendicular to the longitudinal central axis direction of the locking hole 15a is greater than the inner diameter of the locking hole 15a.

When the first bending angle A1 and the second bending angle A2 are not equal, a projection of the second bending portion 143a on the plane perpendicular to the longitudinal central axis direction of the locking hole 15a may partially or all fall into a projection of the first bending portion 142a on the plane perpendicular to the longitudinal central axis direction of the locking hole 15a. When the first bending angle A1 and the second bending angle A2 are equal, the projection of the second bending portion 143a on the plane perpendicular to the longitudinal central axis direction of the locking hole 15a may all fall into the projection of the first bending portion 142a on the plane perpendicular to the longitudinal central axis direction of the locking hole 15a.

It can be understood that in other embodiments, the locking member also may include a number of bending portions. The shape of each bending portion is similar to that of the first bending portion or the second bending portion. The bending portions are connected end to end. The proximal ends of the end-to-end bending portions are connected with the distal end of the connecting portion, and a first bending included angle is formed between the connecting portion and the bending portion closest to the connecting portion. The diameter of a circumscribed circle of a projection of each bending portion on a cross section perpendicular to a lengthwise direction of the bending portion is less than that of a minimum inscribed circle of the locking hole. The width of a projection of a whole formed by the multiple end-to-end bending portions on the plane perpendicular to the longitudinal central axis direction of the locking hole is greater than the diameter of a maximum inscribed circle of the locking hole. The width of a projection of the bending portion, closest to the connecting portion, on the plane perpendicular to the longitudinal central axis direction of the locking hole is greater than the diameter of the maximum inscribed circle of the locking hole.

Figure 7:
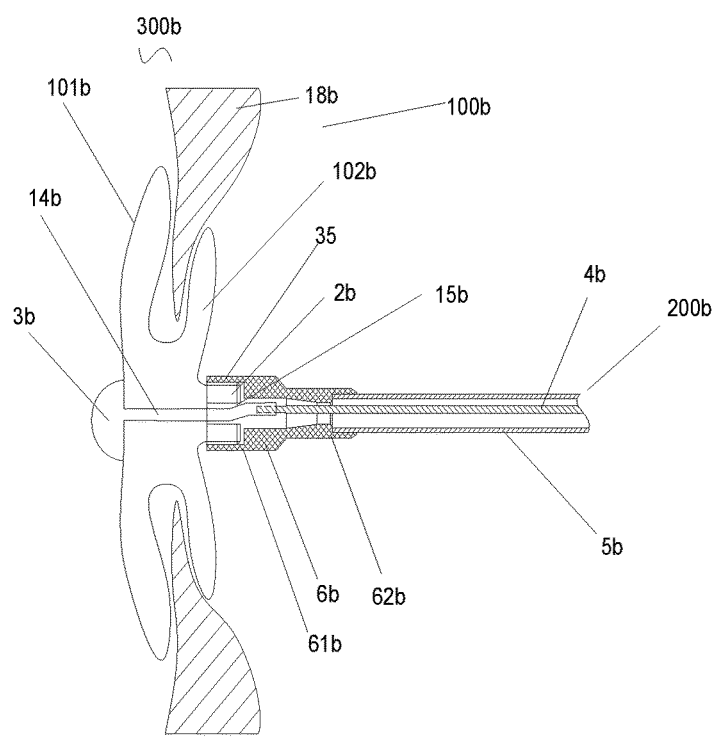
FIG. 7 is a structural schematic diagram of an occlusion device provided in a third exemplary embodiment of the present application.

As shown in FIG. 7, a third exemplary embodiment of the present application further shows an occlusion device 300b. By taking an occluder shown by a second exemplary embodiment, for example, the occlusion device 300b of the present embodiment includes an occluder 100b, a hollow delivery mechanism 200b at least configured with an opening in the distal end, a locking sleeve 6b for connecting the delivery mechanism 200b with the occluder 100b, and a traction member 4b movably accommodated in the delivery mechanism 200b. The distal end of the traction member 4b penetrates the distal end of the delivery mechanism 200b and may be detachably connected with the proximal end of the locking member 14b in a cavity. The traction member 4b may pull the locking member 14b under the action of an external force applied by an operator, such as a doctor, towards the proximal end to drive the distal end of the occluder 100b to move towards the proximal end till the proximal end of the locking member 14b passes through the locking hole 15b and abuts against the end face of the proximal end bolt head 2b to lock the occluder 100b.

The structure of the occluder 100b is completely described in a second exemplary embodiment above, so, for the sake of brevity, no more details will be described here.

Figure 8:
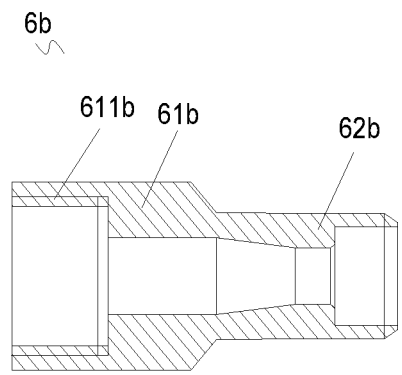
FIG. 8 is a structural schematic diagram of a locking sleeve of the occlusion device in FIG. 7.
Figure 9:
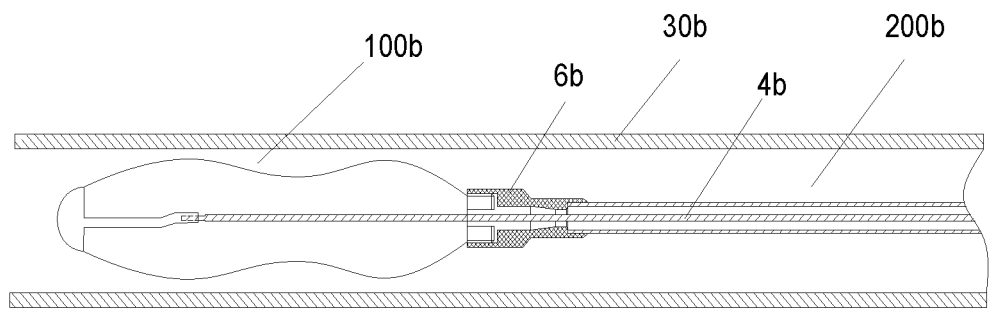
FIG. 9 is a schematic diagram of the occlusion device, located in a sheath tube, in a third exemplary embodiment of the present application.
Figure 10:
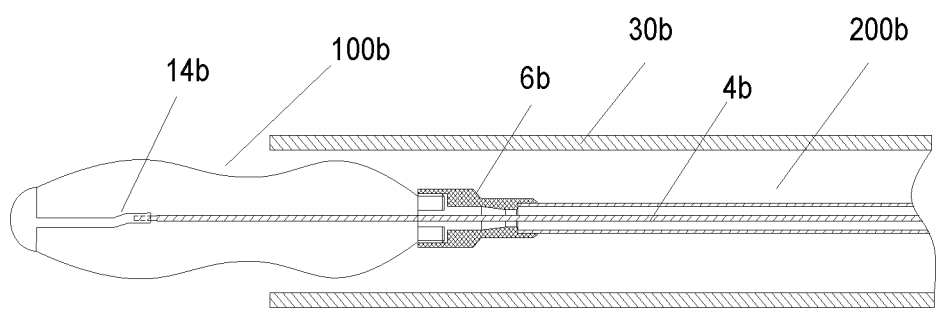
FIG. 10 is a schematic diagram of pushing an occluder in FIG. 9 out of the sheath tube.
Figure 11:
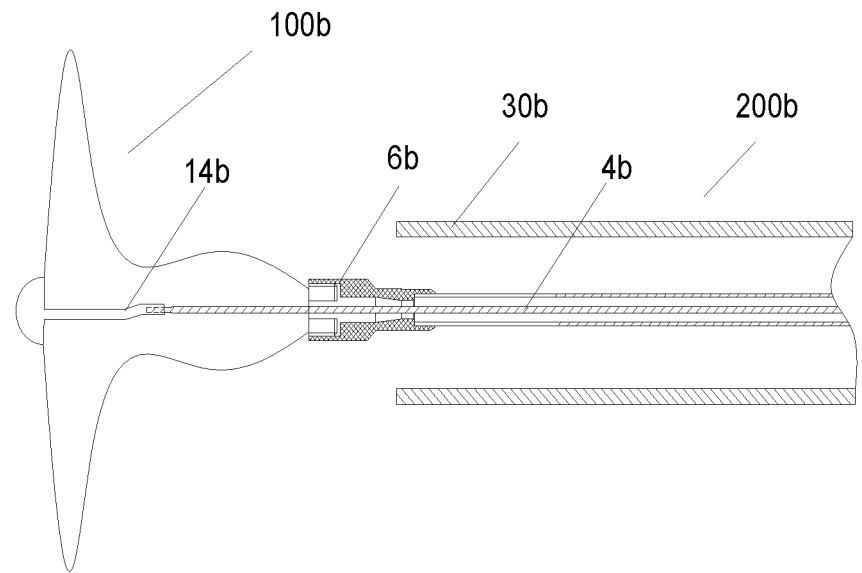
FIG. 11 is a schematic diagram of partially releasing the occluder in FIG. 10.
Figure 12:
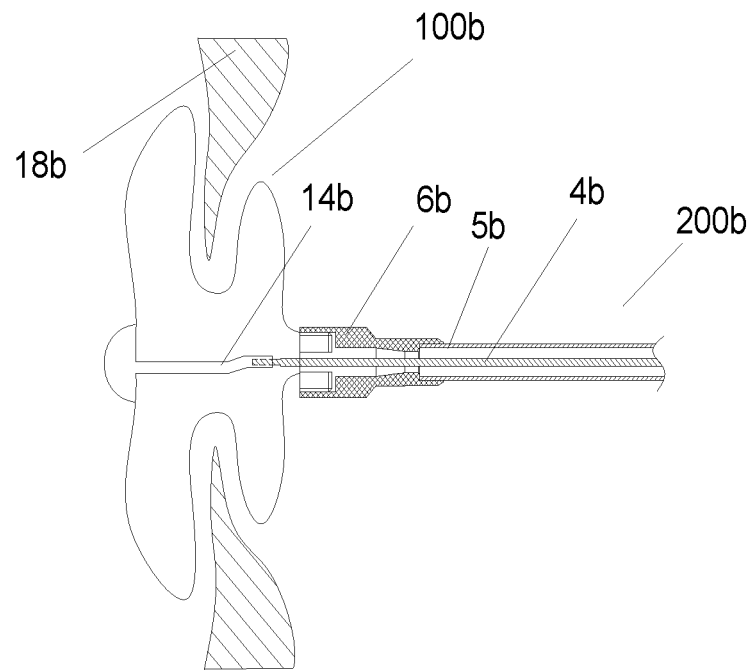
FIG. 12 is a schematic diagram of releasing, but not locking, the occluder in FIG. 11 when the occluder arrives at a defect part.
Figure 13:
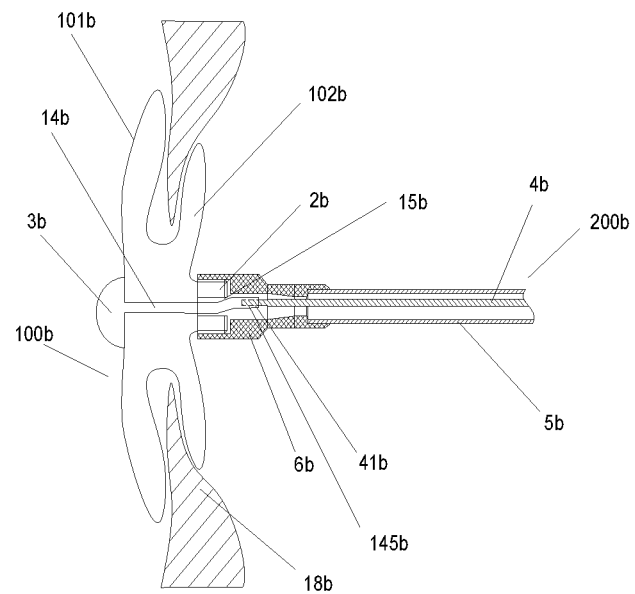
FIG. 13 is a schematic diagram of the occluder in FIG. 12 in a locked state.

Referring to FIG. 8 as well, the locking sleeve 6b is used for connecting the delivery mechanism 200b with the proximal end bolt head 2b of the occluder 100b, and includes a first connecting head 61b and a second connecting head 62b which are connected with each other, and the proximal end of the first connecting head 61b is connected with the distal end of the second connecting head 62b. The first connecting head 61b and the second connecting head 62b are both hollow and communicate with each other. On the whole, the first connecting head 61b and the second connecting head 62b are of barrel shapes. The inner diameter of the first connecting head 61b is greater than that of the second connecting head 62b. The inner surface of the first connecting head 61b is configured with an internal thread 611b matched with the external thread of the proximal end bolt head 2b of the occluder 100b. During connection, the second connecting head 62b is arranged at the distal end of the delivery mechanism 200b in a sleeving manner and the first connecting head 61b is arranged on the proximal end bolt head 2b of the occluder 100b in a sleeving manner through laser welding at first; and the locking sleeve 6b is fastened and connected with the proximal end bolt head 2b by screwing the delivery mechanism 200b.

In the occluder 100b, a locking process is completed by cooperation of the locking member 14b and the proximal end bolt head 2b having the locking hole 15b. The locking member 14b is of a rod-like structure and similar structures, and has a bending angle, so that a locking structure is simple; and no complicated mechanical structure and no cooperation relation are needed, so that a manufacturing process and the locking operation are simplified. Furthermore, after passing through the locking hole 15b and being exposed from the locking hole 15b through elastic deformation, the proximal end of the locking member 14b may abut against the proximal end portion of the locking hole 15b, and the locking is high in reliability and has a low failure rate.

FIGS. 9 to 13 show the cooperation of the occluder 100b and the delivery mechanism 200b to implement delivery, release, and locking processes. First, the occluder 100b and the delivery mechanism 200b are connected together through the locking sleeve 6b, and the locking sleeve 6b and the proximal end bolt head 2b are in threaded connection and collected in a sheath tube 30b. The distal end of the traction member 4b and the locking member 14b are in threaded connection. When the occluder 100b is collected into the sheath tube 30b, the traction member 4b is set along an axial direction of the sheath tube 30b without restraining the free deformation of the occluder 100b.

The occluder 100b is pushed to a heart defect part 18b, and the traction member 4b is pulled towards the proximal end to allow the two disk-shaped structures of the occluder 100b to be closed up gradually to form an "I" shape and implement the state as shown in FIG. 7. The specific process is as follows:

Under the traction of the traction member 4b, the locking member 14b abuts against the locking hole 15b of the proximal end bolt head 2b; as a force exists between the inner wall of the proximal end bolt head 2b and the second bending portion 143b of the locking member 14b, the second bending portion 143b and the first bending portion 142b of the locking member 14b may apply a force to the inner wall of the locking hole 15b along with the insertion of the locking member 14b into the locking hole 15b; the first bending portion 142b and the second bending portion 143b bend under the pressing action of the inner wall of the locking hole 15b, so that the first bending included angle A1 and the second bending included angle A2 are enlarged to allow the widths of the projections of the first bending portion 142b and the second bending portion 143b on the plane perpendicular to the longitudinal central axis direction of the locking hole 15b to be less than the inner diameter of the locking hole 15b and allow the locking member 14b to be continuously inserted into the locking hole 15b; when the distal end of the locking member 14b is exposed from the distal end of the locking hole 15b, the force applied by the inner wall of the locking hole 15b to the first bending portion 142b and the second bending portion 143b disappears gradually, and the first bending portion 142b and the second bending portion 143b gradually recover original shapes; and the width of the projection of the locking member 14b on the plane perpendicular to the longitudinal central axis direction of the locking hole 15b is greater than the inner diameter of the locking hole 15b, and the side surface of the first bending portion 142b abuts against the proximal end face of the locking hole 15b, so that the locking member 14b may not move towards the distal end to complete the locking of the occluder 100b.

The traction member 4b is rotated to relieve the connection with the locking member 14b; after the connection is relieved, the traction member 4b is withdrawn; a delivery tube 5b is rotated to relieve the connection between the locking sleeve 6b and the proximal end bolt head 2b; and finally, the delivery tube 5b is pulled back to complete removal.

As the locking member 14b passes through the locking hole 15b through the elastic deformation, the locking process is reversible. The occluder 100b further has an unlocked state. Before the connection between the traction member 4b and the locking member 14b is not relieved, the traction member 4b may be axially operated to move towards the distal end till the locking member 14b returns back into the cavity of the occluder 100b through the locking hole 15b, then the occluder 100b returns from the state in FIG. 13 to the state in FIG. 11, and the unlocking is realized. After the occluder 100b returns to the state in FIG. 11, the delivery tube 5b may be further pulled towards the proximal end to withdraw the occluder 100b into the sheath tube 30b to implement the withdrawal of the occluder 100b.

All the technical features of the above embodiments may be combined, as desired. To simplify the descriptions, not all possible combinations of all the technical features in the above-mentioned embodiments are described. However, the combinations of these technical features shall all fall within the scope in the present application in case of no contradictions.

The above embodiments only express several implementation modes of the present application, and their descriptions are relatively specific and detailed, but should not be understood as limitations to the application thereby. It should be noted that persons of ordinary skill in the art can also make variety of changes and improvements without departing from the conception of the present application, and these changes and improvements fall within the protection scope of the present application.

The invention claimed is:

1. An occluder, comprising:
   a mesh occlusion body defining a cavity and a proximal end bolt head, and the proximal end bolt head defines a locking hole in communication with the cavity;
   the occluder further comprises a locking member located in the cavity;
   a distal end of the locking member is connected with the distal end of the occlusion body;
   the locking member is an elastic member, and comprises a connecting portion connected with the occlusion body and a first bending portion connected with the proximal end of the connecting portion, wherein the first bending portion is elastic;
   a joint of the connecting portion and the first bending portion defines a first bending included angle, wherein the first bending included angle ranges from 120 degrees to 175 degrees;
   the diameter of a circumscribed circle of a projection of the first bending portion on a cross section perpendicular to the lengthwise direction of the first bending portion is less than that of a minimum inscribed circle of the locking hole; and
   the width of a projection of the first bending portion on a plane perpendicular to the longitudinal central axis direction of the locking hole is greater than the diameter of a maximum inscribed circle of the locking hole.

2. The occluder according to claim 1, wherein the proximal end portion of the locking member is configured with a threaded hole in communication with an outside.

3. The occluder according to claim 2, wherein the threaded hole is coaxial with the bending portion.

4. The occluder according to claim 2, wherein the locking member is a hollow tubular structure, and the threaded hole is in communication with an inner cavity of the locking member.

5. The occluder according to claim 1, wherein the proximal end portion of the locking member is configured with a fillet.

6. The occluder according to claim 1, wherein the proximal end bolt head is configured with an external thread.

7. The occluder according to claim 1, wherein the distal end portion of the locking hole is configured with a transitional region, and an aperture of the distal end of the transitional region is greater than that of the proximal end of the transitional region.

8. The occluder according to claim 1, wherein the occlusion body is made of a macromolecular material biologically compatible.

9. An occluder, comprising:
   a mesh occlusion body defining a cavity and a proximal end bolt head, and the proximal end bolt head defines a locking hole communicated with the cavity;
   the occluder further comprises a locking member located in the cavity;
   a distal end of the locking member is connected with the distal end of the occlusion body;
   the locking member is an elastic member, and comprises a connecting portion connected with the occlusion body and a plurality of bending portions connected with one another end to end, wherein the plurality of bending portions is elastic;
   the proximal ends of the end-to-end bending portions are connected with the proximal end of the connecting portion, and a first bending included angle is formed between the connecting portion and the bending portion closest to the connecting portion;
   the diameter of a circumscribed circle of a projection of each bending portion on a cross section perpendicular to the lengthwise direction of the bending portion is less than that of a minimum inscribed circle of the locking hole; and
   the width of a projection of a whole, formed by the multiple end-to-end bending portions, on a plane perpendicular to the longitudinal central axis direction of the locking hole is greater than the diameter of a maximum inscribed circle of the locking hole.

10. The occluder according to claim 9, wherein the width of a projection of the bending portion, proximate to the connecting portion, on the plane perpendicular to the longitudinal central axis direction of the locking hole, is greater than the diameter of the maximum inscribed circle of the locking hole.

11. The occluder according to claim 10, wherein in end-to-end bending portions, the bending portion closest to the connecting portion is a first bending portion, and the bending portion closest to the first bending portion is a second bending portion; and
    a second bending included angle is formed between the second bending portion and the first bending portion, and the first bending included angle is equal to the second bending included angle.

12. An occlusion device, comprising:
    an occluder comprising a mesh occlusion body defining a cavity and a proximal end bolt head, and the proximal end bolt head defines a locking hole in communication with the cavity;
    the occluder further comprises a locking member located in the cavity;
    a distal end of the locking member is connected with the distal end of the occlusion body;
    the locking member is an elastic member, and comprises a connecting portion connected with the occlusion body and a first bending portion connected with the proximal end of the connecting portion, wherein both the connecting portion and the first bending portion are elastic;
    a joint of the connecting portion and the first bending portion defines a first bending included angle;
    the diameter of a circumscribed circle of a projection of the first bending portion on a cross section perpendicular to the lengthwise direction of the first bending portion is less than that of a minimum inscribed circle of the locking hole; and
    the width of a projection of the first bending portion on a plane perpendicular to the longitudinal central axis direction of the locking hole is greater than the diameter of a maximum inscribed circle of the locking hole; and the occlusion device further comprising a hollow delivery mechanism at least defining an opening in the distal end, a locking sleeve for connecting the delivery mechanism with the occluder, and a traction member movably accommodated in the delivery mechanism, wherein the distal end of the traction member penetrates the distal end of the delivery mechanism and then is detachably connected with the proximal end of the bending portion of the locking member.

13. The occlusion device according to claim 12, wherein the proximal end portion of the locking member is configured with a threaded hole in communication with an outside, and the distal end of the traction member is configured with an external thread matched with the threaded hole of the locking member.

14. The occlusion device according to claim 13, wherein the proximal end bolt head is configured with an external thread; the locking sleeve comprises a hollow first connecting head and a second connecting head connected with the proximal end of the first connecting head; the first connecting head is configured with an internal thread matched with the external thread of the proximal end bolt head; and the second connecting head is arranged on an outer wall of the delivery mechanism in a sleeving manner.

* * * * *